US012584825B2

(12) United States Patent
Moix Olivé

(10) Patent No.: US 12,584,825 B2
(45) Date of Patent: Mar. 24, 2026

(54) ASPIRATING PATHOGEN DETECTION SYSTEM

(71) Applicant: Carrier Fire & Security EMEA BV, Diegem (BE)

(72) Inventor: Pere Moix Olivé, Barcelona (ES)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 512 days.

(21) Appl. No.: 17/707,018

(22) Filed: Mar. 29, 2022

(65) Prior Publication Data

US 2022/0316999 A1 Oct. 6, 2022

(30) Foreign Application Priority Data

Mar. 31, 2021 (EP) .................................... 21382271

(51) Int. Cl.
*G01N 1/22* (2006.01)
*G01N 1/26* (2006.01)
*G01N 21/59* (2006.01)
*G01N 33/00* (2006.01)
*G08B 21/14* (2006.01)
(Continued)

(52) U.S. Cl.
CPC .............. *G01N 1/2273* (2013.01); *G01N 1/26* (2013.01); *G01N 21/59* (2013.01); *G01N 33/0016* (2013.01); *G01N 33/0036* (2013.01); *G08B 21/14* (2013.01); *G08B 21/16* (2013.01);
(Continued)

(58) Field of Classification Search
CPC .......... G01N 1/24; G01N 1/26; G01N 1/2273; G01N 21/59; G01N 33/0016; G01N 33/0036; G01N 2021/5903
See application file for complete search history.

(56) References Cited

U.S. PATENT DOCUMENTS

| | | | |
|---|---|---|---|
| 6,610,977 B2 | 8/2003 | Megerle | |
| 6,834,533 B2 | 12/2004 | Megerle | |

(Continued)

FOREIGN PATENT DOCUMENTS

| | | | |
|---|---|---|---|
| CN | 201716810 U | 1/2011 | |
| CN | 101727727 B | 6/2011 | |

(Continued)

OTHER PUBLICATIONS

Author Unknown, "Aspirating Smoke Detection: Very sensitive and reliable fire detection through differentiation between smoke and deceptive phenomena" Siemens Schweiz Ag; Asd Technology; Jun. 9, 2015; 9 Pages. https://sid.siemens.com/v/u/A6V10583600.

(Continued)

*Primary Examiner* — Nathaniel J Kolb

(74) *Attorney, Agent, or Firm* — CANTOR COLBURN LLP

(57) ABSTRACT

An aspirating detection system for monitoring for the presence of a pathogen, the aspirating detection system including: a network of one or more pipes for sampling air from a plurality of locations monitored by the aspirating detection system; a sensor unit 3 comprising a housing 13 fluidly connected to the network of one or more pipes, and a biosensor 12 mounted within the housing, the biosensor being configured to monitor for the presence of the pathogen; and an aspirator 15 configured to draw airflow through the network of one or more pipes and through the biosensor 12.

12 Claims, 4 Drawing Sheets

(51) Int. Cl.
  *G08B 21/16*      (2006.01)
  *G01N 1/24*       (2006.01)
(52) U.S. Cl.
  CPC ......... *G01N 2001/222* (2013.01); *G01N 1/24* (2013.01); *G01N 2021/5903* (2013.01)

(56)           References Cited

U.S. PATENT DOCUMENTS

|  |  |  |  |  |
|---|---|---|---|---|
| 8,742,939 | B2 | 6/2014 | Polak et al. | |
| 9,576,458 | B2 | 2/2017 | Calvert | |
| 10,746,426 | B2 | 8/2020 | Lakamraju et al. | |
| 11,054,347 | B1 * | 7/2021 | Gogoana .............. | G01N 1/2214 |
| 2010/0186524 | A1 | 7/2010 | Ariessohn et al. | |
| 2012/0162640 | A1 * | 6/2012 | Sakagami ................. | G01J 3/44 |
| | | | | 356/301 |
| 2016/0086468 | A1 * | 3/2016 | Calvert ................ | G08B 29/188 |
| | | | | 340/628 |
| 2019/0287364 | A1 * | 9/2019 | Birnkrant ............. | G08B 17/107 |
| 2020/0109976 | A1 | 4/2020 | Ajay et al. | |
| 2020/0400631 | A1 * | 12/2020 | Gao ........................ | G01N 33/00 |
| 2022/0074857 | A1 * | 3/2022 | Zaghloul .......... | G01N 33/56983 |

FOREIGN PATENT DOCUMENTS

| | | |
|---|---|---|
| CN | 209387621 U | 9/2019 |
| CN | 111094538 A | 5/2020 |
| RU | 2010106563 A | 6/2010 |
| WO | 2007135423 A1 | 11/2007 |
| WO | 2012123936 A2 | 9/2012 |
| WO | 2019142647 A1 | 7/2019 |

OTHER PUBLICATIONS

Author Unknown, "VESDA-E Aspirating Smoke Detection Technology"; Xtralis; Doc. No. 26845_16; Feb. 2021; 8 Pages. https://xtralis.com/file/868.

Author Unknown; "Air-sampling Smoke Detection Combined with Gas Monitoring"; Vesda Eco; Xtralis; date unknown; 4 Pages. https://www.ansul.com/en/us/DocMedia/18911.pdf.

Author Unknown; "Low-Cost Airborne Biological Contaminant Sensor: Real-time Detection of Bacteria, Viruses, and Fungal Spores"; RTI International; Commercialization; date unknown; 2 Pages. https://www.rti.org/brochures/low-cost-airborne-biological-contaminant-sensor-commercialization.

European Search Report for Application No. 21382271.1; Issued Oct. 8, 2021; 7 Pages.

Weinmann, Karin et al. "A New Biosensor for the COVID-19 Virus: Detection in the environment"; Swiss Federal Laboratories for Materials Science and Technology; Apr. 21, 2020; 4 Pages. https://www.sciencedaily.com/releases/2020/04/200421112520.htm.

European Search Report for Application No. 24204344.6, Issued Jan. 31, 2025, 10 Pages.

* cited by examiner

100

Removing a modular sensor unit from an existing aspirating detection system — 103

Fluidly connecting a second sensor unit to the network of pipes of the existing aspirating detection system — 101

Electronically connecting the second sensor unit to a controller of the existing aspirating detection system — 102

ASPIRATING PATHOGEN DETECTION SYSTEM

FOREIGN PRIORITY

This application claims priority to European Patent Application No. EP21382271.1, filed Mar. 31, 2021, and all the benefits accruing therefrom under 35 U.S.C. § 119, the contents of which in its entirety are herein incorporated by reference.

TECHNICAL FIELD OF INVENTION

The present invention relates to aspirating detection systems, and particularly to an aspirating detection system for monitoring for the presence of a pathogen.

BACKGROUND OF THE INVENTION

Aspirating detection systems are most commonly used as smoke detectors, i.e. aspirating detection systems employed for smoke detection in buildings or locations where point smoke detectors may not provide sufficient detection of smoke. Aspirating smoke detectors detect smoke at a centralised detection unit. Aspirating smoke detectors typically draw air from various sampling locations through a network of pipes, the sample air then being analysed to determine if any smoke is present. Accordingly it is understood that an aspirating smoke detector generally comprises a centralised detection unit, and a network of pipes through which air is aspirated to the centralised detection location. Once smoke is detected the aspirating smoke detector generates an alarm, indicating that the sampled environment is compromised.

By using centralised detection, aspirating detectors may sample large areas (e.g. entire and/or multiple floors and rooms of buildings or other structures) with high efficiency and/or accuracy.

SUMMARY OF THE INVENTION

Viewed from a first aspect, the invention provides an aspirating detection system for monitoring for the presence of a pathogen, the aspirating detection system comprising: a network of one or more pipes for sampling air from a plurality of locations monitored by the aspirating detection system; a sensor unit comprising a housing fluidly connected to the network of one or more pipes, and a biosensor mounted within the housing, the biosensor being configured to monitor for the presence of the pathogen; and an aspirator configured to draw airflow through the network of one or more pipes and through the biosensor.

The provision of a sensor unit comprising a biosensor in an aspirating detection system allows for the rapid detection of pathogens in the air of large areas that would be otherwise difficult to monitor, such as public places with limited ventilation and high people turnover (for example, train stations, hospitals, etc.). Improved detection for pathogens, i.e. any organism that can produce disease or infection (including viruses), in such locations will always be desirable in order to achieve safe and healthy environments for people.

The aspirating detection system is able to sample large areas of buildings or structures and monitor for the presence of pathogens with high efficiency and accuracy. As such, the aspirating detection system provides a faster and more reliable system for detecting pathogens.

The biosensor may be configured to monitor for the presence of one or more viruses within a predetermined group of pathogenic viruses. In other embodiments, the biosensor may be configured to monitor for the presence of a single, specific pathogenic virus. In one embodiment, the pathogenic virus or group of predetermined group of pathogenic viruses may comprise the SARS-CoV-2 virus and/or one or more mutation thereof.

The biosensor may comprise a bioreceptor configured to undergo a property change responsive to exposure to the pathogen; and a detector configured to detect the property change of the bioreceptor and produce a signal indicative of the property change.

The bioreceptor may be configured for one or more of the following types of interaction: antibody/antigen, enzymes/ligands, nucleic acids/DNA, nucleic acids/RNA, DNA/RNA, cellular structures/cells and biomimetic materials.

The bioreceptor may be configured to undergo a property change responsive to exposure to viral RNA.

The detector may comprise an electrochemical sensor, electronic sensor, gravimetric sensor, pyroelectric sensor or piezoelectric sensor.

The detector may comprise a light source, such as a laser, configured to illuminate the bioreceptor and an optical sensor configured to detect a change in the optical properties of the light received from the bioreceptor.

The biosensor may comprise a Localised Surface Plasmon Resonance (LSPR) sensor. The LSPR sensor may comprise a bioreceptor, the bioreceptor comprising a plurality of metallic nanostructures, a plurality of biological elements being immobilised on each nanostructure. The LSPR sensor may comprise a light source, such as a laser, configured to illuminate the bioreceptor and an optical sensor.

The illuminating light, from the light source, may be reflected by, refracted by or transmitted through the bioreceptor and received by the optical sensor.

The optical sensor may be configured to detect a change in the absorption spectrum (e.g. wavelength and/or intensity changes) of the received light as a result of a biorecognition event occurring in the bioreceptor.

The sensor unit may comprise a temperature control system configured to regulate a temperature of one or both of the biosensor and the airflow through the sensor unit.

The temperature control system may be configured to maintain the temperature of the airflow at the biosensor at a predetermined temperature, which is preferably a predetermined temperature associated with the pathogen.

The temperature control system may be configured to heat the airflow as it enters the sensor unit so that it reaches a predetermined temperature. The temperature control system may be configured to heat the biosensor as airflow enters the biosensor so that it reaches a predetermined temperature. The temperature control system may comprise a heater configured to heat the airflow and/or the biosensor. The temperature control system may comprise one or more temperature sensor. The one or more temperature sensor may be configured to measure a temperature of the airflow entering the sensor unit and/or upstream of or within the biosensor. The temperature control system may control the heater based on the measured temperature or temperatures.

The predetermined temperature may be selected according to a type of pathogen and/or a type of target analyte of the biosensor.

The predetermined temperature may be based upon a critical temperature associated with the target biological interaction of the biosensor.

For instance, when the biosensor is configured to monitor for the presence of a pathogenic virus, the target analyte may be viral RNA, and the bioreceptor may comprise DNA receptors/molecules. The hybridisation interaction between the DNA and the RNA, wherein complementary strands associate together to form a double helix structure, is highly temperature dependent. Hybridisation cannot occur if the molecules have not been denatured/melted at a specific melting temperature first. Thus, the predetermined temperature may be based on the melting temperature of the specific DNA/RNA interaction.

In another example, the bioreceptor may comprise antibodies configured to bind to an antigen of the pathogen. Accordingly, the predetermined temperature may be based on the temperature of the human body, e.g. a temperature between 30° C. and 45° C., and more preferably between 35° C. and 40° C.

The sensor unit may comprise an information panel. The information panel may comprise a number of buttons, lights or other visual indicators. The information panel may be configured to indicate one or more of an operational state of the sensor unit, a status of the sensor unit and/or a performance of the sensor unit, which may include an operational state, a status and/or a performance of the biosensor and/or the temperature control system. For example, the information panel may be for indicating whether the sensor unit is on, connected to the controller and/or whether there are any faults with the sensor unit itself or its component parts, such as the biosensor and/or the temperature control system.

The sensor unit may be one of a plurality of sensor units of the aspirating detection system. Optionally the plurality of sensor units may comprise additional sensor units configured to measure different properties.

In some embodiments, the plurality of sensor units may further include a (second) sensor unit comprising a sensor configured to monitor for one or more of: the presence of smoke, and the presence of a gas, where the gas may comprise one or more of carbon monoxide, ammonia gas, hydrogen gas, chlorine gas, oxygen, methane gas, and sulphides.

In some embodiments, the plurality of sensor units may further include a (second) sensor unit comprising a biosensor configured to monitor for the presence of a second, different pathogen.

Typically, aspirating detection systems are utilised for determining an alarm condition in a building or structure by monitoring for the presence of smoke and/or the presence of harmful gases (e.g. carbon monoxide). The described aspirating detection system may be achieved by starting from an existing aspirating detection system, i.e. configured to monitor for the presence of a different contaminant (e.g. smoke, carbon monoxide), and modifying it to include the sensor unit comprising the biosensor configured to monitor for the presence of a pathogen.

The provision of the sensor unit comprising a biosensor configured to monitor for the presence of a pathogen in a plurality of sensor units of the aspirating detection system therefore updates and expands the function of the existing installation.

The installation, maintenance and monitoring of multiple detecting systems within a building or location may be expensive and time consuming. The described aspirating detection system provides for the detecting and monitoring of multiple alarm conditions, including the presence of one or more pathogens and the presence of one or more organic or inorganic chemical contaminants, using a single detection system.

The plurality of sensor units of the aspirating detection system may be interchangeable, modular sensor units.

By modular it may be meant that each sensor unit is a separate, discrete module, such that each sensor unit can be independently removed or replaced within the system, optionally without the use of specialist tools. The modular sensor units may be interchangeable. Hence, as a result of the modularity of the sensor units they may be assembled or interchanged easily according to the building requirements and/or owner or occupant requirements. This may be performed without having to change the network of pipes and central controller. This means that a bespoke system may easily be provided. Also, the units may be easily replaced and repaired such that maintenance is facilitated. Thus the system may be easily maintained, repaired, or modified after its installation to maintain and/or update its performance. Optionally the aspirating detector system may be configured to permit future attachment of one or more additional modular sensor unit.

The housing of each sensor unit may be substantially the same. The housing of each sensor unit may have the same shape and/or size of inlets and/or outlets and the inlets and/or outlets may be in the same relative positions for each sensor unit.

The sensor units may be configured to be interchanged with one another without modification to the other sensor units and/or other parts of the system such as the controller and/or pipes. Thus, the modular sensor units may be regarded as interchangeable sensor units. The modular sensor units may be interchanged for one another without changes to their hardware, software, structure, design and/or structure, or other general properties which they may comprise.

The modular sensor units may be interchanged for one another without changes to the hardware, software, structure, design and/or other general properties of the other parts of the detection system such as the controller and/or network of pipes (i.e. sampling pipes).

Each of the plurality of sensor units may be connected to one another in series. That is, being an aspirating detection system, an intake of aspirating air may be configured to (i.e. in use) flow sequentially through each of the plurality of sensor units.

Each of the plurality of sensor units may comprise an inlet and an outlet. The plurality of sensor units may be connected to each other in series via the inlet and outlet of each of the plurality of sensor units. The inlet of one of the plurality of sensor units may be connected to the outlet of an upstream and adjacent sensor unit. Additionally or alternatively, the outlet of one of the plurality of sensor units may be connected to the inlet of a downstream and adjacent sensor unit.

The inlet of an upstream sensor unit may be connected to an intake portion of the aspirating detection system. The intake portion of the aspirating detection system may receive air from a network of one or more pipes. Additionally and/or alternatively, the outlet of a downstream sensor unit may be connected to an exhaust of the aspirating detection system.

Connecting the plurality of modular sensor units to one another as discussed may facilitate the installation and/or removal of the one or more of the plurality of modular sensor units from the central detection unit. Connecting the plurality of modular sensor units in series may ease the maintenance and installation of the central detection unit/aspirating detection system. Additionally and/or alternatively, requiring that each of the plurality of modular sensor units is connected in a similar manner may simplify the manufacture of the modular sensor units and may simplify the installation and customisability of the aspirating detecting system, owing to the modular one-size-fits-all approach of the system. Simplification of these processes may result in reduced costs and time taken to perform these processes.

The sensor units may alternatively be connected in parallel. The aspirating detection system may comprise a manifold. The manifold may be for directing air from the network of pipes to the sensor units.

The aspirating detection system may be configured so that modular sensor units can be connected and/or disconnected, e.g. added, removed or interchanged, without affecting the other modular sensor units.

The aspirating detection system may comprise interconnecting pipes for connecting between the modular sensor units. The interconnecting pipes may be in fixed positions to allow the sensor units to be interchanged easily. The interconnecting pipes may be flexible.

The inlet of each modular sensor unit may be regarded as upstream of its outlet, whilst the outlet may be regarded as downstream of its inlet, as in most systems where there is a flow. As it will be readily appreciated for an aspirating detection system, the flow is a fluid flow. The fluid flow is preferably in a gaseous phase. The fluid may be sampled air from the building, i.e. air drawn in through the network of one or more pipes.

Upstream may be regarded as the direction in which a fluid, such as air, is initially aspirated into the central detection unit/aspirating detection system, whilst downstream may be regarded as the direction in which the fluid, such as air, is finally exhausted from the central detection unit/aspirating detection system.

The connecting of each of the plurality of modular sensor units, as described herein, may be regarded as connecting the modular sensor units such that an aspirated fluid may flow through the plurality of modular sensor units, e.g. in series. The plurality of modular sensor units may be in flow communication with one another. The plurality of modular sensor units may be in flow communication with one another in series.

The aspirating detection system may comprise a network of one or more pipes, a controller and the one or more sensor units. The or each sensor unit may be connected to the same network of one or more pipes and/or the same controller.

The provision of a common controller in the aspirating detection system may centralise the control of the aspirating detection system. Accordingly, the output from the or each sensor unit may be collated at a single output point, which may comprise a data output for transmitting digital data and/or a visual interface panel of the system configured to display the data to an operator. This may facilitate monitoring of the building or structure.

The or each sensor unit may be controlled by the common controller.

The system may comprise one or more information panel. This may be a common information panel or an information panel may be provided on each sensor unit. The information panel may comprise a number of buttons, lights or other visual indicators. The information panel may be for indicating the operation, status and/or performance of the or each sensor unit. For example, the information panel may be for indicating whether the sensor unit is on, connected to the controller and/or whether there are any faults with the sensor unit itself.

The controller may be suitable for receiving an input (e.g. data) from each of the one or more sensor units. The input from each of the one or more sensor units may be one or more signals. Accordingly, the input received by the controller may correspond to the sensing of the presence of one or more contaminants (e.g. pathogen, smoke, carbon monoxide) sensed by the one or more sensor units. The input received from each sensor unit may correspond to the detected presence of a different contaminant. This is because each sensor unit may be configured to monitor for the presence of a different contaminant.

The controller may be in electronic communication with each of the one or more sensor unit(s). The electronic communication may be wired communication and/or wireless communication. The wireless communication may be performed by a number of protocols, including but not limited to infrared, WiFi, radio, Bluetooth or other known wireless forms of communication.

The controller may comprise a processor. The processor may be configured to generate an alarm signal when the presence of one or more contaminants is detected by the one or more sensor units. The processor may be configured to receive the input from each of the one or more sensor units. The controller may be configured to process (e.g. using the processor) the input (e.g. data) from each of the one or more sensor units.

The controller may be programmed so that it can process the input from a number of different sensor units. The controller may be arranged so that the software can be adjusted as required if the one or more sensor units are interchanged and/or additional sensor units are added. In this way, the sensor unit(s) may be chosen and/or interchanged without having to modify, e.g. reprogram, the controller.

The controller may be a control unit, i.e. a module that is discrete from the modular sensor units. The controller may be housed in a control panel unit. The control panel unit may comprise any one or more of the controller, the processor, and one or more devices which facilitate the electronic communication of each of the one or more sensor units with the controller. The control panel unit may comprise a screen or other visual indicator displaying current properties and/or a status of the controller. The control panel unit may comprise an aural or visual indicator with which the status of the monitoring and/or detection of the presence of one or more contaminants, including the presence of a pathogen, may be indicated.

The system may comprise a single control panel for reporting the status of the one or more sensor units.

The aspirating detection system is configured to aspirate air from a plurality of locations in the environment to be monitored by the aspirating detection system. To aspirate air from the plurality of locations, an aspirator (i.e. air moving device), such as one or more pumps and/or one or more fans may be provided, each configured to aspirate air. The one or more pumps and/or one or more fans may be provided downstream or upstream of the sensor unit(s).

Additionally or alternatively, one or more or each of the one or more sensor units may be provided with an aspirator, e.g. a pump and/or a fan. The aspirator of each sensor unit may be switched on or off as required. In an aspirating detection system with a plurality of aspirators (e.g. an aspirator in each one of a plurality of sensor units), each aspirator may be independently operable and/or controllable.

By providing one or more independently operable and/or controllable aspirators within one or more sensor units the total airflow speed within the aspirating detection system may be adjusted, e.g. optimised. For example, each of the one or more aspirators (e.g. fans and/or pumps) may each generate a static pressure. The total pressure generated by the aspirating detection system for aspirating air may be regarded as the sum of the static pressures of each of the aspirators. As such the pressure generated and/or the total airflow speed may be adjusted by interchanging the sensor unit(s) and/or by controlling, e.g. powering on or off, the aspirators as required. This may be used to achieve a desired airflow rather than using bigger or unnecessary aspirators (e.g. fans and/or pumps). This may allow a balance between maximising the energy efficiency of the system whilst achieving a desired coverage area and/or sample transit time of the system.

For example, if the aspirating detection system has a relatively short network of one or more pipes (e.g. in a prison cell), the system may be operated with only one aspirator on. Any other aspirators in the system may be off. If the aspirating detection system has a relatively long network of one or more pipes (e.g. in a shopping centre/mall or an airport), the system may be operated with many, or all of the aspirators on, as required.

The aspirating detection system may comprise a single aspirator for directing sampled air through each of the sensor unit(s).

In an aspirating detection system with a plurality of sensor units, the sensor units may sample the same intake of aspirated air independently of one another. That is, the plurality of sensor units may sample the same intake of aspirated air without affecting the properties of the sample. As the sensor units may be provided in series, the sample or air aspirated by the system may pass through each of the plurality of sensor units. As the outlet of one sensor unit may act as the inlet of another, all air samples aspirated may be passed through each sensor. Accordingly, the monitoring for the presence of a contaminant (e.g. a pathogen, smoke, carbon monoxide) by one sensor unit of the plurality of sensor units may not impact the monitoring and/or detection performed by the other sensor units.

The or each aspirator may be independently adjusted to provide a desired airflow speed through the or each sensor unit of the aspirating detection system.

The sensor unit may comprise one or more air control devices to regulate airflow to the biosensor. The air control device may provide a separate airflow to the biosensor, which may be slower or faster than the total airflow speed of the aspirating detection system. The one or more air control devices may comprise one or more valves and one or more airflow branches, in which one the biosensor may be mounted.

While the total airflow speed through the or each sensor unit may be optimised depending on the requirements of the aspirating detection system, the airflow through the biosensor (or other sensor) may be adjusted based on the sensor requirements. For example, certain sensors (e.g. a biosensor) may require more time for analysis of aspirated air samples, and hence require a lower airflow speed or flow rate. Therefore, by providing branch points and valves in the airflow path of the sensor unit, the airflow provided to the biosensor (or other sensor) may be precisely controlled.

Viewed from a second aspect, the invention provides a method of operating an aspirating detection system, the method comprising: drawing a plurality of air samples from a plurality of locations into a network of one or more pipes that direct the air samples to a sensor unit; and monitoring for the presence of a pathogen in the plurality of air samples using a biosensor of the sensor unit.

The method may further comprise regulating a temperature of the plurality of air samples to maintain their temperatures at a predetermined temperature associated with the pathogen.

The method may further comprise directing the plurality of air samples to a second sensor unit; and monitoring for the presence of smoke in the air samples using a sensor of the second sensor unit.

Viewed from a third aspect, the invention provides a method of adapting an existing aspirating detection system to detect the presence of a pathogen, the existing aspirating detection system comprising a network of one or more pipes for sampling air from a plurality of locations monitored by the aspirating detection system; a first sensor unit comprising a housing fluidly connected to the network of one or more pipes, and an aspirator configured to draw airflow through the network of one or more pipes and through the first sensor unit, the method comprising: fluidly connecting a second sensor unit to the network of one or more pipes of the aspirating detection system, the second sensor unit comprising a biosensor configured to monitor for the presence of the pathogen.

The second sensor unit may be a modular sensor unit and the existing aspirating detection system may comprise at least one modular sensor unit.

The step of fluidly connecting the modular sensor unit to the aspirating detection system may comprise interchanging the modular sensor unit with an existing modular sensor unit of the aspirating detection system.

Viewed from a fourth aspect, the invention provides a sensor unit comprising: a housing configured to be fluidly connected to a network of one or more pipes of an aspirating detection system; a biosensor mounted within the housing and configured to monitor for the presence of a pathogen in an airflow received from the network of one or more pipes; and an aspirator configured to draw the airflow through the network of one or more pipes and through the biosensor.

The sensor unit of the fourth aspect of the invention may be the sensor unit of the first aspect of the invention. The sensor unit of the fourth aspect may therefore have one or more or all of the features (including optional features) of the sensor unit of the first aspect.

The biosensor may be configured to monitor for the presence of one or more viruses within a predetermined group of pathogenic viruses.

The biosensor may comprise a bioreceptor configured to undergo a property change responsive to exposure to the pathogen; and a detector configured to measure the property change of the bioreceptor and produce a signal indicative of the property change.

The biosensor may comprise a Localised Surface Plasmon Resonance (LSPR) sensor.

The sensor unit may comprise a temperature control system configured to regulate a temperature of the airflow through the sensor unit.

The sensor unit of the fourth aspect may be for adapting an existing (i.e. pre-installed) aspirating detection system to provide the aspirating detection system of the first aspect.

This may be achieved by the method of the third aspect.

This may be achieved by replacing an existing modular sensor unit of the existing aspirating detection system with the sensor unit of the fourth aspect. Alternatively, this may be achieved by fluidly connecting the sensor unit of the fourth aspect to the existing modular sensor unit of the aspirating detection system.

Modifying an existing aspirating detection system instead of installing a whole new system may reduce manufacture and installation costs of the aspirating detection system.

BRIEF DESCRIPTION OF THE DRAWINGS

Certain example embodiments of the invention will now be described by way of example only and with reference to the accompanying drawings in which.

DETAILED DESCRIPTION OF THE INVENTION

Figure 1:
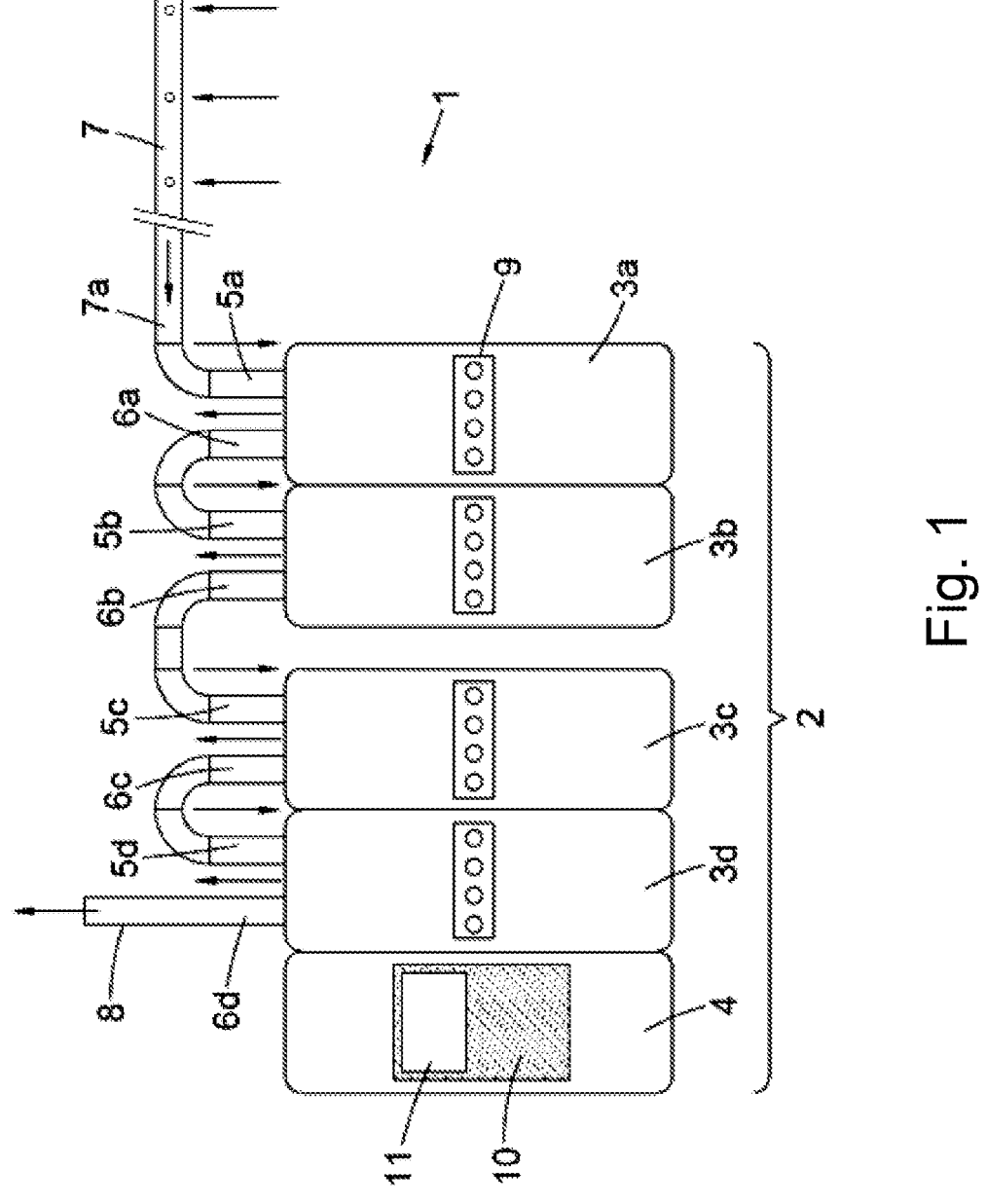
FIG. 1 shows an aspirating detection system.

FIG. 1 shows an aspirating detection system 1 comprising a central detection unit 2 and a network of one or more pipes 7. The network of one or more pipes 7 comprises one or more pipes that are for sampling air from a plurality of locations within the building or structure being monitored by the system 1. Air is aspirated through the network of one or more pipes 7 to the inlet pipe 7a which directs the air sample to the central detection unit 2. The air is exhausted from the aspirating detection system 1 via an exhaust 8.

The central detection unit 2 comprises a plurality of sensor units 3 and a controller 4 (shown as a control unit 4 in FIG. 1). Each of the plurality of sensor units 3 has an inlet 5 and an outlet 6. Each sensor unit 3 also comprises an information panel 9. The panel 9 may comprise a number of buttons, lights or other visual indicators, which notify a user of the operational state and/or performance of the sensor unit 3. The aspirating detection system 1 shown in FIG. 1 comprises four modular sensor units 3a, 3b, 3c, 3d. However, whilst four modular sensor units 3a, 3b, 3c, 3d are illustrated, the aspirating detection system may comprise one, or more, sensor units 3, as required. Furthermore, the one or more sensor units 3 of the aspirating detection system 1 may not be modular.

The arrows in FIG. 1 indicate a direction of flow of the aspirated air during normal operation and, as will be appreciated, the air flows from an inlet 5 of each sensor unit 3 through the sensor unit 3 to an outlet 6 of each sensor unit 3. As such, the network of pipes 7 and inlet pipe 7a are upstream of the modular sensor units 3, whilst the exhaust 8 is downstream of the sensor units 3. Accordingly, the central detection unit 2 may be regarded as having an upstream modular sensor unit 3a, which is the most upstream or first modular sensor unit 3a. Similarly, the central detection unit 2 may be regarded as having a downstream modular sensor unit 3d, which is the most downstream or last modular sensor unit 3d. The upstream modular sensor unit 3a is connected to the network of pipes 7 via inlet pipe 7a and its inlet 5a. The downstream modular sensor unit 3d is connected to the exhaust 8 by its outlet 6d.

It is to be appreciated that if the aspirating detection system 1 comprises a single sensor unit 3, that the inlet 5 of the single sensor unit 3 is to be connected to the network of pipes 7 via inlet pipe 7a, whilst the outlet 6 of the single sensor unit 3 is to be connected to the exhaust 8.

As can be seen in the example embodiment shown in FIG. 1, the modular sensor units 3 are connected in series. The outlet 6a of the first modular sensor unit 3a is connected to the inlet 5b of a second modular sensor unit 3b. The second modular sensor unit 3b is downstream and adjacent to the first modular sensor unit 3a. Conversely, the first modular sensor unit 3a is upstream and adjacent to the second modular sensor unit 3b. The outlet 6b of the second modular sensor unit 3b is connected to the inlet 5c of the third modular sensor unit 3c. The outlet 6c of the third modular sensor unit 3c is connected to the inlet 5c of the fourth modular sensor unit 3d. Accordingly, it may be seen that the inlet 5 of each of the modular sensor units 3 is connected to the outlet 6 of an upstream and adjacent modular sensor unit 3. Conversely, the outlet 6 of each of the modular sensor units 3 is connected to the inlet of a downstream and adjacent modular sensor unit.

The flow follows the connections made between the inlets 5 and outlets 6 of each of the modular sensor units 3. As such, the flow of aspirated air through the modular sensor units 3 is continuous, and thus the modular sensor units 3 are in series with one another.

The aspirating detection system 1 may include a controller 4 arranged to receive an input from each of the modular sensor units 3. The controller 4 is not in flow communication with the modular sensor units 3, but is in electrical communication with the modular sensor units 3. The electrical communication may be conveyed by a wireless or a wired connection. Wireless connections may comprise known wireless communication methods such as Wi-Fi, radio, infrared, Bluetooth, or other known wireless communication protocols. The controller 4 includes a control panel 10, which may comprise inputs such as buttons, a touch screen, or otherwise, for programming and/or controlling the controller 4, the central detection unit 2 and/or the sensor units 3. A display 11 is also included to inform a user of the operation and/or control options of the controller 4, the central detection unit 2 and/or the sensor units 3. The controller 4 may be regarded as being housed in a control panel unit. The controller 4 centralises the operations of the modular sensor units 3. The modular sensor units 3 may be interchanged as and when required. This may include for maintenance purposes such as servicing or repair, or to customise the central detection unit 4. The interchange of sensor units 3 may be performed without having to adjust the controller 4.

Figure 2:
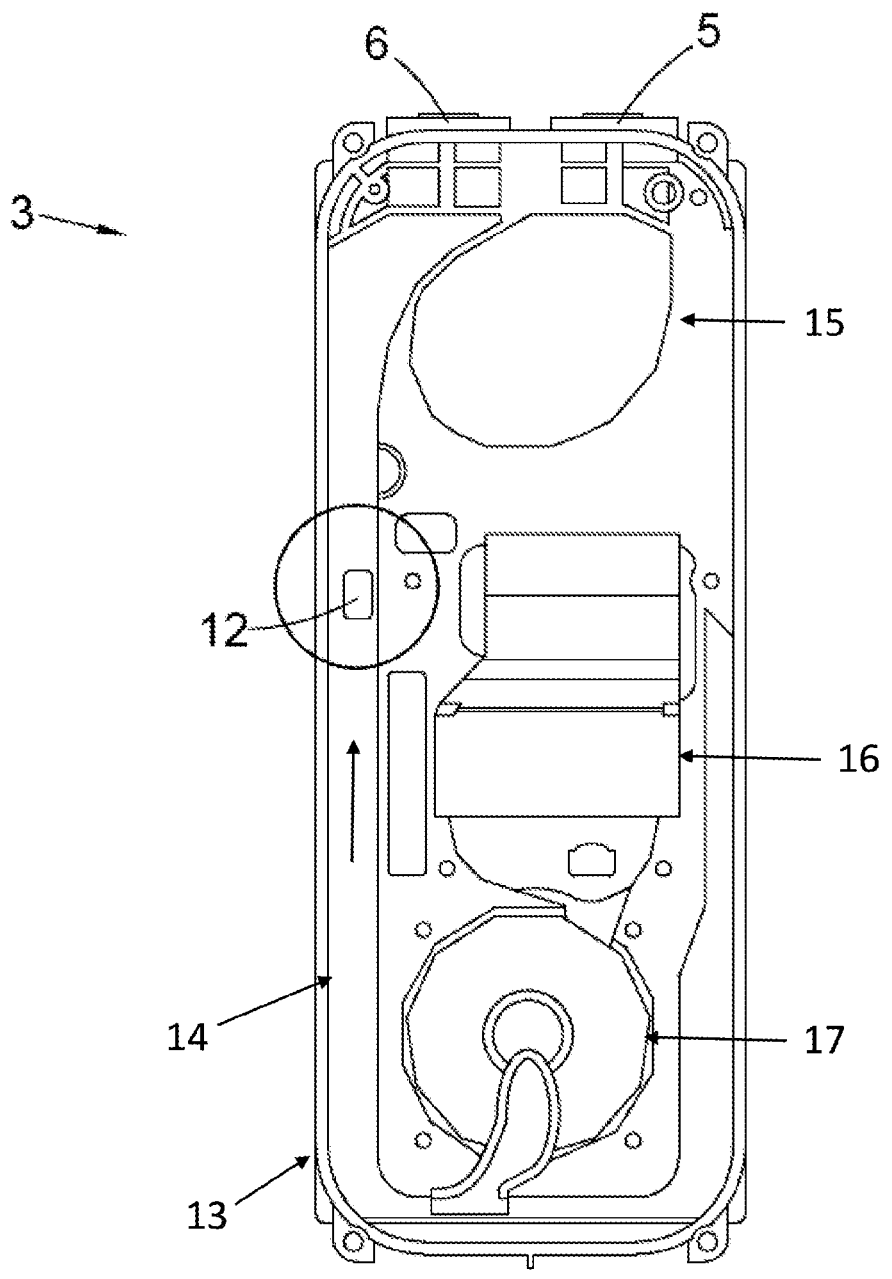
FIG. 2 shows a sensor unit.

FIG. 2 shows the internal structure of a sensor unit 3. As the described aspirating detection system 1 comprises a plurality of modular sensor units 3 (as illustrated in FIG. 1), the structure and composition of the single sensor unit 3 illustrated in FIG. 2 may apply to one or more of the modular sensor units 3a, 3b, 3c, 3d.

The sensor unit 3 of the aspirating detection system 1 comprises a housing 13. The housing 13 is fluidly connected to the network of one or more pipes via an inlet 5 and an outlet 6. The internal structure of the housing 13 is configured to receive the components of the sensor unit 3 and to provide an internal flow path 14 from the inlet 5 to the outlet 6.

In the described embodiment, the aspirator 15 (i.e. air moving device, such as one or more pumps and/or one or more fans) is mounted inside the housing 13 of the sensor unit 3, preferably proximate to the inlet 5, and configured to move air along the internal flow path 14 from the inlet 5 to the outlet 6. However, the aspirator 15 may not necessarily be provided in the housing 13 of the sensor unit 3 but may be located downstream or upstream of the sensor unit 3.

The sensor unit 3 also comprises a biosensor 12 mounted within the housing 13. Preferably, the biosensor 12 is mounted in the internal flow path 14 so that aspirated air samples may flow directly through/over the biosensor 12. The biosensor 12 is configured to monitor for the presence of a pathogen in the aspirated air. Accordingly, the biosensor 12 may be configured to monitor for the presence of any type of infectious organism or agent, such as one of the following: a virus, bacterium, protozoan, prion, viroid, fungus or parasite.

The biosensor 12 may be configured to monitor for the presence of one or more pathogens within a predetermined group pathogens (e.g. selected and/or genetically related pathogens). Particularly, the biosensor 12 may be configured to monitor for the presence of one or more pathogenic viruses within a predetermined group of pathogenic viruses. For example, viruses of the same family/genus, having similar genetic material and/or antigens, may be detected by a single biosensor 12. In one embodiment, the biosensor 12 may be configured to monitor for the presence of a group of pathogenic viruses comprising the SARS-CoV-2 virus and/or one or more mutation thereof.

The sensor unit 3 may also comprise electronic components 16. The electronic components 16 may include a sensor unit controller, wherein the biosensor 12 is in electronic communication with and/or controlled by the sensor unit controller. The sensor unit controller may be configured to receive and process a signal received from the biosensor 12 and raise an alarm signal when the presence a pathogen is detected by the biosensor 12. Alternatively or additionally, the sensor unit controller (electronic components 16) may be configured to receive and/or transmit a signal from/to the controller 4.

The sensor unit 3 may also comprise a temperature control system 17 configured to regulate a temperature of the airflow in the internal flow path 14 and/or a temperature of the biosensor 12. The temperature control system 17 may be configured to maintain the temperature of the airflow and/or the temperature of the biosensor 12 at a predetermined temperature associated with the pathogen. The temperature control system 18 may heat the airflow and/or the biosensor 12 so that it reaches a predetermined temperature. This predetermined temperature may be selected according to the type of pathogen and type of analyte that is to be targeted, as discussed later in relation to FIGS. 3a and 3b.

The temperature control system 17 may comprise a heater (not shown) configured to heat the airflow in the flow path 14 and/or the biosensor 12. The temperature control system 17 may comprise one or more temperature sensor (not shown). The one or more temperature sensor may be configured to measure a temperature of the airflow entering the sensor unit 3, and/or a temperature of the flow path 14 upstream of the biosensor 12, and/or a temperature within the biosensor 12. The temperature control system 17 may control the heater based on the measured temperature or temperatures.

The temperature control system 17 may be in electronic communication with and/or controlled by the controller 4 via electronic components 16.

Where the aspirating detection system 1 comprises a plurality of sensor units 3a-3d, one or more or each of the plurality of sensor units 3a-3d may be provided with an aspirator 15. The aspirator 15 of each sensor unit 3 may be switched on or off as required. Where the aspirating detection system 1 comprises a plurality of aspirators 15 (e.g. an aspirator 15 in each one of a plurality of sensor units 3a-3d), each aspirator 15 may be independently operable and/or controllable.

The provision of an aspirator within each sensor unit 3 permits simple installation of the modular system, as any combination of sensor units 3 may be assembled as each unit 3 comprises its own aspirator.

Furthermore, by providing an independently operable and/or controllable aspirator 15 within each sensor unit 3 the total airflow speed within the aspirating detection system 1 may be adjusted, e.g. optimised, for the particular sensor of the sensor unit 3.

For example, it may be desired to slow down or speed up airflow as it passes over/through a sensor of a sensor unit 3, such as biosensor 12. Sensors may require different time periods for analysis of an air sample—for example, biosensors 12 may require slightly more time to analyse air samples for the presence of a pathogen in comparison to smoke sensors. Thus, alternatively or additionally, the sensor unit 3 may comprise one or more air control devices (not shown), such as one or more valves, to isolate an air sample in the biosensor 12 of the sensor unit 3 from the airflow of the aspirating detection system 1.

Figures 3A, 3B:
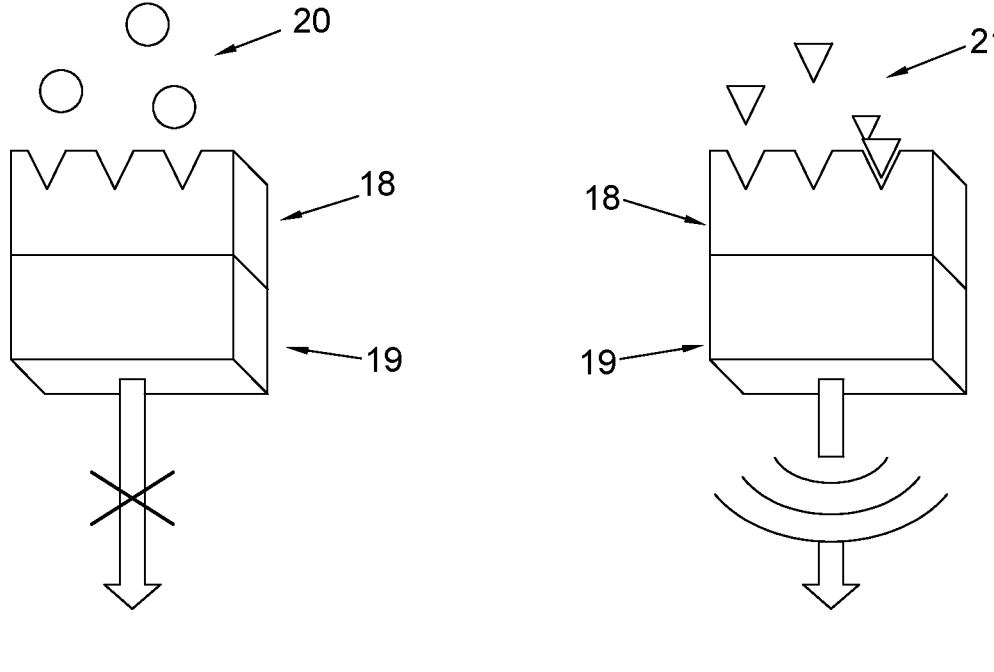
FIG. 3a shows a biosensor when not in the presence of a target pathogen.
FIG. 3b shows a biosensor when in the presence of a target pathogen.

The function of an example biosensor 12 is shown schematically in FIGS. 3a and 3b. The biosensor 12 comprises a bioreceptor 18 and a detector 19.

The bioreceptor 18 is configured to undergo a property change responsive to exposure to the pathogen. In other words, the bioreceptor 18 is configured to interact with an analyte of interest (target analyte 21), the bioreceptor 18 providing high specificity and selectivity for the target analyte 21, in that it will not interact with different analytes 20. As such, the bioreceptor 18 may comprise a plurality of biological elements selected to interact (e.g. bind) with the molecules of the target analyte 21. The bioreceptor 18 may be configured for one or more of the following types of interaction: antibody/antigen, enzymes/ligands, nucleic acids/DNA, nucleic acids/RNA, DNA/RNA, cellular structures/cells or biomimetic materials. The interaction of the one or more biological elements with the molecules of the target analyte 21 produces an effect or property change in the bioreceptor 18 measurable by the detector 19.

The biosensor 12 may comprise one or more bioreceptors 18.

The detector 19 is configured to detect the property change of the bioreceptor 18 and produce a signal indicative of the property change. The detector 19 is associated with the bioreceptor 18 in a controlled manner. The signal produced by the detector 19 may be proportionate to the concentration of the analyte.

The detector 19 may comprise an electrochemical sensor configured to detect a change in one or more of a current, potential, charge, impedance or conductance of the bioreceptor 18 as a result of a biorecognition event (e.g. an interaction with a target analyte 21) occurring in the bioreceptor 18.

The detector 19 may comprise an electronic sensor, gravimetric sensor, pyroelectric sensor or piezoelectric sensor.

The detector 19 may comprise a light source (e.g. laser) configured to illuminate the bioreceptor 18 and an optical sensor, the optical sensor configured to detect a change in the optical properties of the light as a result of a biorecognition event (e.g. an interaction with a target analyte 21) occurring in the bioreceptor 18.

Figure 3C:
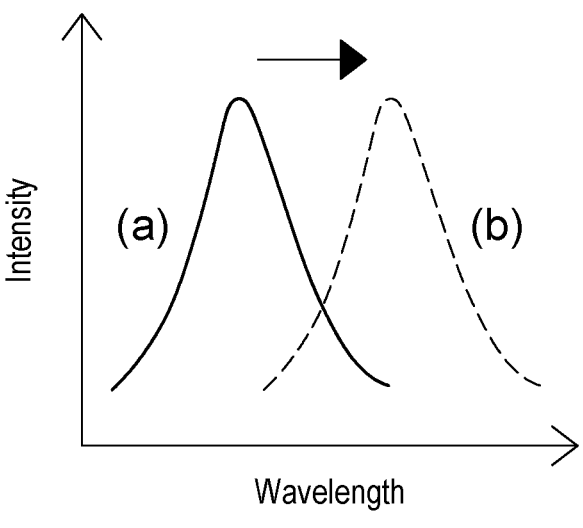
FIG. 3c shows a property change of a biosensor responsive to exposure to a target pathogen.

For example, in an embodiment, the biosensor 12 may comprise a Localised Surface Plasmon Resonance (LSPR) biosensor, a form of optical biosensor. In an LSPR biosensor 12, the bioreceptor 18 comprises metallic nanostructures (MNPs) immobilised on a substrate (e.g. a glass slide or optical fibre) or suspended in solution. A plurality of biological elements are immobilised on the surface of the MNPs. The LSPR biosensor 12 comprises a light source (e.g. laser) which illuminates the bioreceptor 18. When the incident light interacts with the MNPs, the electromagnetic field of the light induces collective electron charge oscillations locally in the metallic nanostructures and the subsequent absorbance of light within the ultraviolet-visible (UV-VIS) band. When an interaction between a biological element of a MNP and a target analyte molecule (e.g. binding event) occurs, the absorption spectrum of the bioreceptor 18 changes. The 'wavelength-shift' (see FIG. 3c) may be detected by an optical sensor of the LSPR biosensor, and the optical sensor produces a signal indicative of the property change in the absorption spectrum of the bioreceptor 18, and the signal is passed to the controller 4.

By way of example, the biosensor 12 may include the dual-functional LSPR biosensor as discussed in Qiu, G., Gai, Z., Tao, Y., Schmitt, J., Kullak-Ublick, G. A., and Wang, J; "Dual-Functional Plasmonic Photothermal Biosensors for Highly Accurate Severe Acute Respiratory Syndrome Coronavirus 2 Detection". ACS Nano. 2020. DOI: 10.1021/acsnano.0c02439.

The detection of the presence of a pathogen using a biosensor 12 (specifically the bioreceptor 18 interaction, e.g. binding of biological elements of the bioreceptor 18 with the molecules of the target analyte 21) may be highly dependent on environmental parameters, such as temperature.

For example, where the biosensor 12 is configured to monitor for the presence of a pathogenic virus, the target analyte 21 may be viral RNA, e.g. a specific RNA strand of the virus genome. Accordingly, the bioreceptor 18 therefore may comprise one or more DNA receptors (e.g. DNA ligands). The or each DNA receptor comprises a sequence of nucleic acid molecules (nucleotides) complementary to the target viral RNA strand (e.g. analyte 21).

The interaction of the bioreceptor 18 may therefore be hybridisation between the DNA receptors and the viral RNA, i.e. the RNA will associate to DNA that has a complementary nucleotide sequence to form a double helix. This hybridisation interaction between the DNA and the RNA, wherein complementary strands associate together to form a double helix structure, is highly temperature dependent—particularly, hybridisation cannot occur if any double helix molecules have not initially been denatured/melted at a specific 'melting temperature' first.

Thus, with reference to FIG. 2, the temperature control system 18 may be configured to regulate a temperature of the airflow and/or the biosensor 12. In an embodiment, the temperature control system 18 may be configured to raise the temperature of the airflow and/or the biosensor 12 to a predetermined temperature (e.g. based on the melting temperature of the specific DNA/RNA interaction). The temperature control system 18 may be configured to subsequently lower the temperature of the airflow and/or the biosensor 12 to below the predetermined temperature (e.g. allow it to fall, in order to encourage the hybridisation of the RNA analyte 21 to the DNA receptors after denaturation).

In a different embodiment, the bioreceptor 18 may comprise antibodies configured to bind to an antigen 21 of the pathogen. Accordingly, the temperature control system 18 may be configured to maintain a predetermined temperature based on the temperature of the human body, e.g. a temperature between 30° C. and 45° C., and more preferably between 35° C. and 40° C. As such, the temperature control system 18 may be configured to regulate a temperature of the biosensor 12 in accordance with the type of bioreceptor 18 interaction.

In the described aspirating detection system 1, comprising a plurality of modular sensor units 3a-d (as illustrated in FIG. 1), at least one modular sensor unit (for example, modular sensor unit 3a) comprises a biosensor 12.

One or more of the remaining modular sensor units 3b, 3c, 3d may not comprise a biosensor 12, but may comprise a different type of sensor instead. The sensor may be configured to detect and/or monitor for the presence of one or more contaminants in the aspirated air samples. The sensor may be one of the following: a smoke sensor, a carbon monoxide sensor, a carbon monoxide sensor, an ammonia gas sensor, a hydrogen gas sensor, a chlorine gas sensor, a fluorine gas sensor, an oxygen gas sensor, a methane gas sensor, or a sulphide gas sensor. The sensor may be an industrial organic chemical sensor, configured to detect gases such as formaldehyde, toluene, xylenes, acetone, isobutylene, octane, or alcohols. The sensor may be a flammable gas sensor, configured to detect target gases such as hydrocarbon gas, liquid petroleum gas, natural gas, propane, pentane, or R410a. The sensor may be an indoor air quality sensor, and as such may be configured to detect target odours, carbon dioxide, or other undesirable gas compounds.

One or more of the remaining modular sensor units 3b, 3c, 3d may comprise a biosensor 12 configured to monitor for the presence of a (second) pathogen different from the pathogen of the biosensor 12 of modular sensor unit 3a. The second biosensor 12 may be configured to monitor for the presence of one or more pathogens within a predetermined second group of pathogens. The second biosensor 12 may be configured to monitor for the presence of one or more pathogenic viruses within a second predetermined group of pathogenic viruses.

The remaining modular sensor units 3b, 3c, 3d may not comprise a biosensor 12, or another sensor, but may be a dummy sensor unit not comprising any sensors. The dummy sensor units may provide for a continuation of the flow path for the sampled air. For example, the dummy sensor may be a housing which is the same as the housing for the other sensor units but just with internal pipes for connecting the inlet to the outlet.

Each of the modular sensor units 3 may comprise a different sensor. Whilst the modular sensor unit 3 is shown comprising a single sensor, biosensor 12, the or each modular sensor unit 3 may comprise a plurality of sensors and/or biosensors 12.

Figure 4:
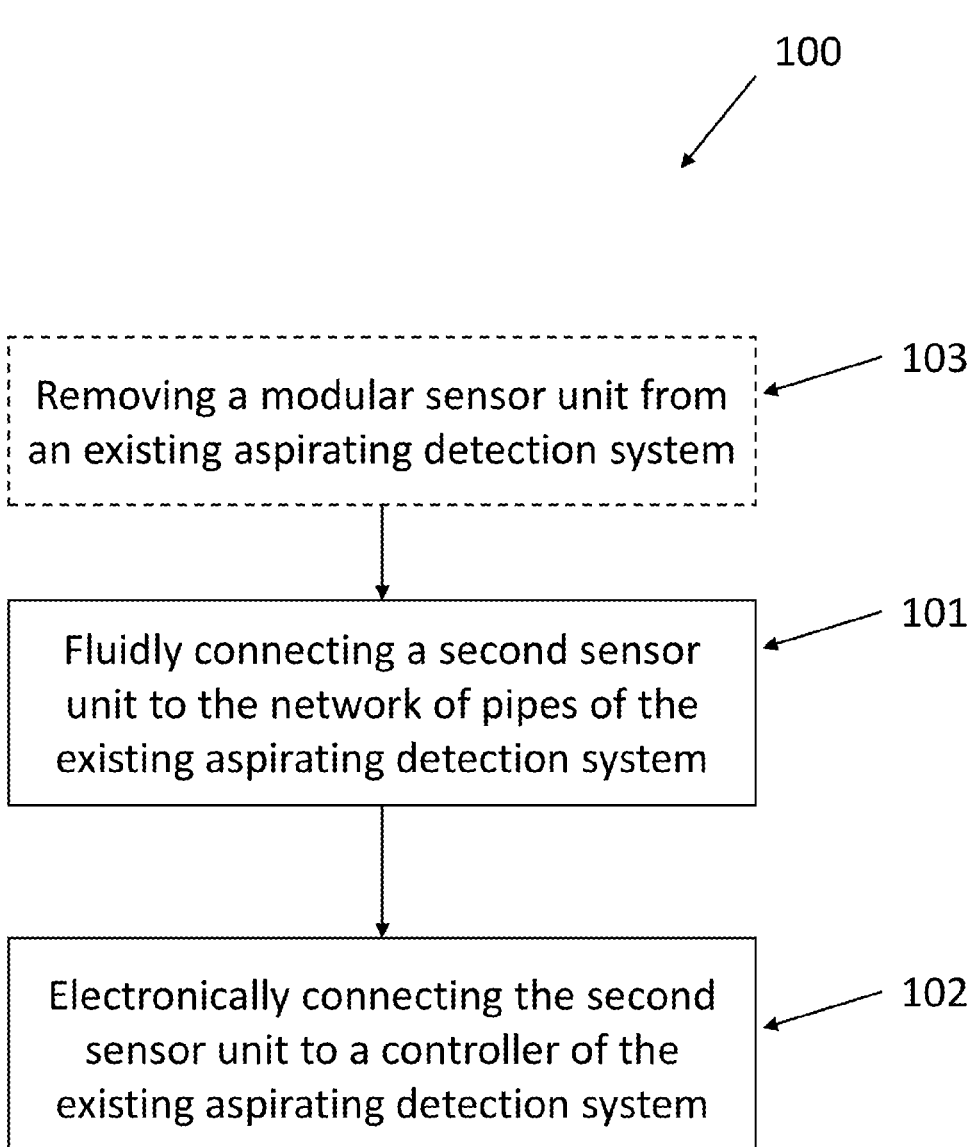
FIG. 4 shows a method of adapting an existing aspirating detection system to monitor for the presence of a pathogen.

The aspirating detection system 1 shown in FIG. 1 may be achieved by retrofitting a sensor unit 3 comprising a biosensor 12 into an existing aspirating detection system. A method 100 of adapting an existing aspirating detection system to monitor for the presence of a pathogen, is now described, as shown in FIG. 4.

The existing aspirating detection system comprises an existing network of one or more pipes 7 for sampling air from a plurality of locations monitored by the aspirating detection system, a first sensor unit 3b comprising a housing fluidly connected to the network of pipe(s), and an aspirator configured to draw airflow through the network of one or more pipes 7 and through the first sensor unit 3b.

The method 100 of adapting (e.g. updating, modifying, retrofitting) the existing aspirating detection system comprises fluidly connecting 101 a second sensor unit 3a to the network of one or more pipes 7 of the aspirating detection system, the second sensor unit 3a comprising a biosensor 12 configured to monitor for the presence of the pathogen.

The step of fluidly connecting 101 the second sensor unit 3a to the network of one or more pipes 7 of the aspirating detection system may comprise connecting the second sensor unit 3a in series or in parallel with the first sensor unit 3b.

The method may further comprise connecting 102 a controller 4 of the existing aspirating detection system to the second sensor unit 3a.

Where the existing aspirating detection system is a modular aspirating detection system (i.e. it comprises at least one modular sensor unit 3a-3d), and the second sensor unit 3a is a modular sensor unit, the step of fluidly connecting 101 the second sensor unit 3a to the aspirating detection system may comprise interchanging the modular second sensor unit 3a with an existing modular sensor unit 3a-3d of the aspirating detection system.

Interchanging the modular sensor unit 3 with an existing modular sensor unit 3a-3d may comprise removing 103 an existing modular sensor unit 3a-3d from the existing aspirating detection system.

Adapting an existing aspirating detection system in this manner may result in an aspirating detection system 1 as described above with reference to FIG. 1.

What is claimed is:

1. An aspirating detection system for monitoring for the presence of a pathogen, the aspirating detection system comprising:
a network of one or more pipes for sampling air from a plurality of locations monitored by the aspirating detection system;
a plurality of sensor units; and
one or more aspirators configured to draw airflow through the network of one or more pipes and through the sensor units;
wherein the plurality of sensor units comprises:
a first sensor unit comprising:
a first housing fluidly connected to the network of one or more pipes; and
a sensor mounted within the first housing and configured to monitor for one or more of: the presence of smoke, the presence of carbon monoxide, the presence of ammonia gas, the presence of hydrogen gas, the presence of chlorine gas, the presence of oxygen, the presence of methane gas, and the presence of sulphides; and
a second sensor unit comprising:
a second housing fluidly connected to the network of one or more pipes;
a biosensor mounted within the second housing and configured to monitor for the presence of the pathogen, and
an air control device mounted within the second housing and arranged to provide a separate regulated airflow to the biosensor, wherein the airflow speed of the airflow provided to the biosensor is slower or faster than the total airflow speed of the airflow through the second sensor unit;
wherein the plurality of sensor units are arranged in series having an inlet of one of the plurality of sensor units connected to an outlet of an upstream and adjacent sensor unit.

2. An aspirating detection system as claimed in claim 1, wherein the biosensor is configured to monitor for the presence of one or more viruses within a predetermined group of pathogenic viruses.

3. An aspirating detection system as claimed in claim 1, wherein the biosensor comprises a bioreceptor configured to undergo a property change responsive to exposure to the pathogen; and a detector configured to detect the property change of the bioreceptor and produce a signal indicative of the property change.

4. An aspirating detection system as claimed in claim 3, wherein the biosensor comprises a Localised Surface Plasmon Resonance (LSPR) sensor.

5. An aspirating detection system as claimed in claim 1, wherein the second sensor unit comprises a temperature control system configured to regulate a temperature of the airflow through the second sensor unit.

6. An aspirating detection system as claimed in claim 5, wherein the temperature control system is configured to maintain the temperature of the airflow at a predetermined temperature associated with the pathogen.

7. An aspirating detection system as claimed in claim 1, wherein the plurality of sensor units further includes a sensor unit comprising a biosensor configured to monitor for the presence of a second, different pathogen.

8. An aspirating detection system as claimed in claim 1, wherein the plurality of sensor units of the aspirating detection system are interchangeable, modular sensor units.

9. A method of operating an aspirating detection system, the aspirating detection system comprising: a network of one or more pipes for sampling air from a plurality of locations monitored by the aspirating detection system; a plurality of sensor units, each sensor unit comprising a housing fluidly connected to the network of one or more pipes; and one or more aspirators configured to draw airflow through the network of one or more pipes and through the sensor units; wherein the plurality of sensor units comprises: a first sensor unit comprising a first housing fluidly connected to the network of one or more pipes, and a sensor mounted within the first housing; and a second sensor unit comprising a second housing fluidly connected to the network of one or more pipes, a biosensor mounted within the second housing, and an air control device mounted within the second housing; the method comprising:
drawing a plurality of air samples from a plurality of locations into the network of one or more pipes that direct the air samples to the plurality of sensor units;
monitoring for one or more of: the presence of smoke, the presence of carbon monoxide, the presence of ammonia gas, the presence of hydrogen gas, the presence of chlorine gas, the presence of oxygen, the presence of methane gas, and the presence of sulphides in the plurality of air samples using the sensor of the first sensor unit; and
monitoring for the presence of a pathogen in the plurality of air samples using the biosensor of the second sensor unit, wherein monitoring for the presence of a pathogen in the plurality of air samples comprises using the air control device, mounted within the housing of the second sensor unit, to provide a separate regulated airflow to the biosensor, wherein the airflow speed of the airflow provided to the biosensor is slower or faster than the total airflow speed of the airflow through the second sensor unit;
wherein the plurality of sensor units are arranged in series having an inlet of one of the plurality of sensor units connected to an outlet of an upstream and adjacent sensor unit.

10. A method as claimed in claim 9, further comprising:
regulating a temperature of the plurality of air samples to maintain their temperatures at a predetermined temperature associated with the pathogen.

11. A method of adapting an existing aspirating detection system to monitor for the presence of a pathogen, the existing aspirating detection system comprising a network of one or more pipes for sampling air from a plurality of locations monitored by the aspirating detection system; a first sensor unit comprising a first housing fluidly connected to the network of one or more pipes and a sensor mounted within the first housing and configured to monitor for one or more of: the presence of smoke, the presence of carbon monoxide, the presence of ammonia gas, the presence of hydrogen gas, the presence of chlorine gas, the presence of oxygen, the presence of methane gas, and the presence of sulphides; and one or more aspirators configured to draw airflow through the network of one or more pipes and through the first sensor unit, the method comprising:

fluidly connecting a second housing of a second sensor unit to the network of one or more pipes of the aspirating detection system, the second sensor unit comprising: a biosensor mounted within the second housing and configured to monitor for the presence of a pathogen, and an air control device mounted within the second housing and arranged to provide a separate regulated airflow to the biosensor, wherein the airflow speed of the airflow provided to the biosensor is slower or faster than the total airflow speed of the airflow through the second sensor unit;

wherein the first sensor unit and the second sensor unit are arranged in series having an inlet of one of the plurality of sensor units connected to an outlet of an upstream and adjacent sensor unit.

12. A method as claimed in claim 11, wherein the second sensor unit is a modular sensor unit and the existing aspirating detection system comprises at least one modular sensor unit; and wherein the step of fluidly connecting the second sensor unit to the aspirating detection system comprises interchanging the modular second sensor unit with an existing modular sensor unit of the aspirating detection system.

\*    \*    \*    \*    \*